(12) United States Patent
Wang (10) Patent No.: US 7,700,289 B2
(45) Date of Patent: Apr. 20, 2010

(54) METHOD FOR LABELING RNA

(75) Inventor: Hui Wang, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/397,067

(22) Filed: Apr. 3, 2006

(65) Prior Publication Data

US 2007/0231806 A1 Oct. 4, 2007

(51) Int. Cl.
*C12Q 1/68* (2006.01)
(52) U.S. Cl. .......................................................... 435/6
(58) Field of Classification Search .............. 435/91.21, 435/6
See application file for complete search history.

(56) References Cited

U.S. PATENT DOCUMENTS

| | | | |
|---|---|---|---|
| 4,661,450 A | 4/1987 | Kempe et al. | |
| 5,573,913 A | 11/1996 | Rosemeyer et al. | |
| 5,659,025 A | 8/1997 | Engels et al. | |
| 5,985,567 A | 11/1999 | Rampal | |
| 6,218,142 B1 | 4/2001 | Wassenegger et al. | |
| 6,344,316 B1 * | 2/2002 | Lockhart et al. | 435/6 |
| 6,579,707 B2 * | 6/2003 | Fitzgerald et al. | 435/188 |
| 6,992,180 B1 | 1/2006 | Engelhardt et al. | |
| 2001/0014446 A1 | 8/2001 | Heroux et al. | |
| 2002/0197621 A1 * | 12/2002 | Drmanac | 435/6 |
| 2003/0190661 A1 | 10/2003 | Gruber et al. | |
| 2006/0160096 A1 | 7/2006 | Cole et al. | |
| 2006/0172317 A1 | 8/2006 | Wang | |
| 2007/0026411 A1 | 2/2007 | Wang et al. | |

FOREIGN PATENT DOCUMENTS

| | | |
|---|---|---|
| WO | WO 94/12518 | 6/1994 |
| WO | WO 97/27317 A1 | 7/1997 |
| WO | WO 2005/054466 A2 | 6/2005 |

OTHER PUBLICATIONS

Cole et al., Nucleic acids Research, vol. 32, No. 11, e86, pp. 1-9, 2004.*
Romaniuk et al, Methods in Enzymology, vol. 11, pp. 52-59, 1983.*
Roche Laboratories, Technical data sheet, Cat. No. 1 758 250, version 2, Jan. 2003, pp. 1-2.*
Invitrogen, Technical data sheet, Cat. No. 18009-019, rev. date. Jul. 14, 2003, pp. 1-4.*
Finke et al., Biotechniques, vol. 14, No. 3, pp. 448-453, 1993.*
Buainain et al. Journal of Basic Microbiology, vol. 38, No. 2, pp. 85-94, 1998.*
Johnson et al. Kinetic Analysis of Macromolecules, A Pratical Approach, Oxford University Press, vol. 257, pp. 68-69, 2003.*
Ularich Lehmann and Hans Kreipe. Real-time PCR analysis of DNA and RNA Extracted from Formalin-fixed and Praffin-Embedded Biopsies, Real-Time PCR and Archival Biopsies, a Companion to Methods in Enzymology, Academic Press, NY, NY, US vol. 25, No. 4, Dec. 2001 pp. 409-412, XP00230656.
Cosstick et al., "Fluorescent labeling of tRNA and oligodeoxynucleotides using T4 RNA ligase", *Nucleic Acids Research*, 12(4):1791-1810 (1984).
Barrio et al., "Synthesis of Modified Nucleoside 3', 5'-Bisphosphates and their Incorporation into Oligoribonucleotides with T4 RNA Ligase", *Modified Oligoribunucleotides*, 17(11):2077-2081 (1978).
Wang et al., "Direct and sensitive miRna profiling from low-input total RNA", vol. 13, Nov. 14, 2006, pp. 1-9, XP002408565.
Lohman et al., "Mutations in Hepatitis C virus RNAs Conferring Cell Culture Adaptation", *Journal of Virology*, 75(3):1437-1449 (2001).
Richardson et al., "Biotin and fluorescent labeling of RNA using T4 RNA ligase", *Nucleic Acids Research*, 11(18):6167-6184 (1983).
England et al., "Enzymatic Oligoribonucleotide Synthesis with T4 RNA Ligase", American Chemical Society and reprinted by permission of the copyright owner, Reprinted from Biochemistry, 1978, pp. 2070-2076.
England et al., "3'-Terminal Labeling of RNA with T4 RNA Ligase", *Nature*, 275:560-561 (1978).
Bare et al., "Specific substitution into the anticodon loop of yeast tyrosine transfer RNA", *Biochemistry*, 25(19):5825-5830 (1986).
Bruce et al., "Reactions at the termini of tRNA with T4 RNA ligase", *Nucleic Acids Research*, 5(10):3665-3677 (1978).
Patents Act 1977; Search Report under Section 17(5); Date of Search: Jul. 18, 2006.
EP Application No. 06 253 554.7 Search Report and Opinion, dated Nov. 28, 2006.

* cited by examiner

*Primary Examiner*—Gary Benzion
*Assistant Examiner*—Cynthia B Wilder (57) ABSTRACT

Novel methods for labeling RNA in a sample are described, as well as methods of performing an array analysis of a labeled RNA sample.

13 Claims, 1 Drawing Sheet

Fig._1

METHOD FOR LABELING RNA

RELATED APPLICATIONS

Related subject matter is disclosed in U.S. patent application Ser. No. 11/048,225 filed on Jan. 31, 2005 by Wang.

FIELD OF THE INVENTION

The invention relates generally to methods of biochemical analysis. More specifically, the invention relates to providing a method of attaching an observable label to RNA.

BACKGROUND OF THE INVENTION

Straightforward and reliable methods for simultaneously analyzing several constituents of a complex sample are extremely desirable. Polynucleotide arrays (such as DNA or RNA arrays) are known and are used, for example, as diagnostic or screening tools. Such arrays include regions of usually different sequence polynucleotides ("capture agents") arranged in a predetermined configuration on a support. The arrays are "addressable" in that these regions (sometimes referenced as "array features") have different predetermined locations ("addresses") on the support of array. The polynucleotide arrays typically are fabricated on planar supports either by depositing previously obtained polynucleotides onto the support in a site specific fashion or by site specific in situ synthesis of the polynucleotides upon the support. After depositing the polynucleotide capture agents onto the support, the support is typically processed (e.g., washed and blocked for example) and stored prior to use.

In use, an array is contacted with a sample or labeled sample containing analytes (typically, but not necessarily, other polynucleotides) under conditions that promote specific binding of the analytes in the sample to one or more of the capture agents present on the array. Thus, the arrays, when exposed to a sample, will undergo a binding reaction with the sample and exhibit an observed binding pattern. This binding pattern can be detected upon interrogating the array. For example all target polynucleotides (for example, DNA) in the sample can be labeled with a suitable label (such as a fluorescent compound), and the label then can be accurately observed (such as by observing the fluorescence pattern) on the array after exposure of the array to the sample. Assuming that the different sequence polynucleotides were correctly deposited in accordance with the predetermined configuration, then the observed binding pattern will be indicative of the presence and/or concentration of one or more components of the sample. Techniques for scanning arrays are described, for example, in U.S. Pat. No. 5,763,870 and U.S. Pat. No. 5,945,679. Still other techniques useful for observing an array are described in U.S. Pat. No. 5,721,435.

Since the discovery of the biological activity of short interfering RNAs (siRNAs) over a decade ago, so called "small RNAs" (i.e., short non-coding regulatory RNAs that have a defined sequence) have become a subject of intense interest in the research community. See Novina et al., Nature 430: 161-164 (2004). Exemplary small RNAs include siRNAs, microRNAs (miRNAs), tiny non-coding RNAs (tncRNAs) and small modulatory RNAs (smRNAs), as well as many others.

Although the exact biological functions of most small RNAs remain a mystery, it is clear that they are abundant in plants and animals, with up to tens of thousands of copies per cell. For example, to date, over 78 Drosophila microRNA species and 300 human microRNA species have been identified. The levels of the individual species of small RNA, in particular microRNA species, appear to vary according to the developmental stage and type of tissue being examined. It is thought that the levels of particular small RNAs may be correlated with particular phenotypes, as well as with the levels of particular messenger RNAs and proteins. Further, viral microRNAs have been identified, and their presence has been linked to viral latency (see Pfeffer et al., Science, 304: 734-736 (2004)).

The sequences of several hundred miRNAs from a variety of different species, including humans, may be found at the microRNA registry (Griffiths-Jones, Nucl. Acids Res. 2004 32:D109-D111), as found at the world-wide website of the Sanger Institute (Cambridge, UK) (which may be accessed by typing "www" followed by ".sanger.ac.uk/cgi-bin/Rfam/ mirna/browse.pl" into the address bar of a typical internet browser). The sequences of all of the microRNAs deposited at the microRNA registry, including more than 300 microRNA sequences from humans (see Lagos-Quintana et al, Science 294:853-858 (2001); Grad et al, Mol Cell 11: 1253-1263 (2003); Mourelatos et al, Genes Dev 16:720-728 (2002); Lagos-Quintana et al, Curr Biol 12:735-739 (2002); Lagos-Quintana et al, RNA 9:175-179 (2003); Dostie et al, RNA 9:180-186 (2003); Lim et al, Science 299:1540 (2003); Houbaviy et al, Dev Cell 5:351-358 (2003); Michael et al, Mol Cancer Res 1:882-891 (2003); Kim et al, Proc Natl Acad Sci USA 101:360-365 (2004); Suh et al, Dev Biol 270:488-498 (2004); Kasashima et al, Biochem Biophys Res Commun 322:403-410 (2004); and Xie et al, Nature 434:338-345 (2005)), are incorporated herein by reference. MicroRNAs (miRNAs) are a class of single stranded RNAs of approximately 19-25 nt (nucleotides) in length.

Analytic methods employing polynucleotide arrays have been used for investigating these small RNAs, e.g. miRNAs have become a subject of investigation with microarray analysis. See, e.g., Liu et al., Proc. Nat'l Acad. Sci. USA, 101: 9740-9744 (2004); Thomson et al., Nature Methods, 1:1-7 (2004); and Babak et al., RNA, 10: 1813-1819 (2004).

Polynucleotide arrays are also used in the characterization of cellular gene expression. Gene expression analysis involves detection of different mRNA species in a test population and the quantitative determination of different mRNA levels in that test population. Such analytic methods may be used to investigate differential expression between different tissue types, different stages of cellular growth or between normal and diseased states. In typical methods, an RNA sample from a test population and an RNA sample from a control population are distinguishably labeled. A polynucleotide array is then contacted with both test and control RNA samples. Ratios of the distinguishable labels detected on the polynucleotide array provide information on relative expression of different mRNA species in the test and control samples.

Methods of labeling RNAs are of interest for use in array analysis of RNA to provide an observable label used in interrogating the array. In the study of Liu et al., miRNA was transcribed into DNA with a biotin-labeled primer. This primer was subsequently labeled with streptavidin-linked Alexa dye prior to array hybridization. This method is susceptible to any reverse-transcriptase reaction bias. Further, the streptavidin-dye as well as streptavidin-biotin-RNA stochiometry may be difficult to quantify. In the study of Thomson et al., the miRNA was directly labeled with 5'-phosphate-cytidyl-uridyl-Cy3-3' using T4 RNA ligase. This reaction is sensitive to the acceptor sequence. See England et al., Biochemistry, 17: 2069-2776 (1978). In the study of Babak et al (4), the miRNA was labeled with Ulysis Alexa Fluor system, which reacts with guanine residue (G) of RNA. Since different miRNAs do not have uniform G content, this method is not quantitative.

Thus, there is a continuing need for methods of labeling RNA with an observable label. Such methods may be used in conjunction with analytical methods based on observing the label, such as array-based analysis of polynucleotides.

SUMMARY OF THE INVENTION

The invention thus relates to novel methods for labeling RNA in a sample. In particular embodiments, the invention provides methods in which a sample including RNA is contacted with an enzyme having RNA phosphatase activity to provide dephosphorylated RNA. The enzyme having RNA phosphatase activity is then inactivated to provide a resultant solution including the dephosphorylated RNA and inactivated enzyme, the inactivated enzyme no longer having RNA phosphatase activity. The resultant solution is contacted with an enzyme having an RNA ligation activity in the presence of a labeled substrate. This is done under conditions sufficient to result in coupling of the labeled substrate to the RNA in the sample to provide labeled RNA. In typical embodiments, the resultant solution is contacted with the enzyme having RNA ligation activity under conditions that include a DMSO concentration in the range from about 20% to about 30%. The labeled substrate typically includes an observable label moiety attached to a nucleotide moiety.

Methods of performing an array analysis of an RNA sample are also taught herein. In certain embodiments, the invention provides a method of performing an array analysis wherein the method includes labeling the RNA in the sample to provide labeled RNA, as disclosed herein. The labeled RNA is then contacted with an array under conditions sufficient to provide for specific binding of labeled RNA to the array. The array typically is then interrogated to provide data on binding of RNA in the sample to the array.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates embodiments of the present invention.

To facilitate understanding, identical reference numerals have been used, where practical, to designate corresponding elements that are common to the Figures. Figure components are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. Similarly, reference to "an RNA" includes a plurality of different identity (sequence) RNA species.

Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. In this specification and in the claims that follow, reference will be made to a number of terms that shall be defined to have the following meanings unless a contrary intention is apparent.

"Optional" or "optionally" means that the subsequently described circumstance may or may not occur, so that the description includes instances where the circumstance occurs and instances where it does not. For example, if a step of a process is optional, it means that the step may or may not be performed, and, thus, the description includes embodiments wherein the step is performed and embodiments wherein the step is not performed (i.e. it is omitted).

An "oligonucleotide" is a molecule containing from 2 to about 100 nucleotide subunits. The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948, 902 and the references cited therein) which can hybridize with naturally occurring nucleic acids in a sequence specific manner analogous to that of two naturally occurring nucleic acids, e.g., can participate in Watson-Crick base pairing interactions. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking moieties.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A moiety is generally bound to one or more other moieties to provide a molecular entity. As a simple example, a hydroxyl moiety bound to an ethyl moiety provides an ethanol molecule. At various points herein, the text may refer to a moiety by the name of the most closely related structure (e.g. an oligonucleotide moiety may be referenced as an oligonucleotide, a mononucleotide moiety may be referenced as a mononucleotide). However, despite this seeming informality of terminology, the appropriate meaning will be clear to those of ordinary skill in the art given the context, e.g. if the referenced term has a portion of its structure replaced with another group, then the referenced term is usually understood to be the moiety. For example, a mononucleotide moiety is a single nucleotide which has a portion of its structure (e.g. a hydrogen atom, hydroxyl group, or other group) replaced by a different moiety (e.g. a linking group, an observable label moiety, or other group). Similarly, an oligonucleotide moiety is an oligonucleotide which has a portion of its structure (e.g. a hydrogen atom, hydroxyl group, or other group) replaced by a different moiety (e.g. a linking group, an observable label moiety, or other group). "Nucleotide moiety" is generic to both mononucleotide moiety and oligonucleotide moiety.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 1%, at least about 2%, at least about 5%, at least about 10%, at least about 20%, at least about 30%, at least about 50%, at least about 80%, or at least about 90% of the sample (excluding solvents). For example, a sample of isolated RNA (an "isolated RNA sample") typically refers to a sample of RNA obtained using an RNA purification protocol on a starting mixture that include the RNA desired to be purified. An "isolated RNA sample" typically comprises at least about 2% total RNA, or at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, affinity chromatography, and sedimentation according to density. In typical embodiments, one or more of the sample, the enzyme having an RNA ligation activity, and the labeled substrate is in isolated form; more typically, all three are obtained in isolated form prior to use in the present methods. A "purification step" references any method used to increase the relative amount of a desired component in a mixture by removing other components of the mixture and recovering a resultant mixture that is enriched in the desired component.

The term "sample" as used herein relates to a material or mixture of materials, typically, although not necessarily, in fluid form, containing one or more components of interest.

The term "analyte" is used herein to refer to a known or unknown component of a sample. In certain embodiments of the invention, an analyte may specifically bind to a capture agent on a support surface if the analyte and the capture agent are members of a specific binding pair. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). A "target" references an analyte.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

The term "specific binding" refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the binding constant of a capture agent and analyte is greater than $10^6$ $M^{-1}$, greater than $10^7$ $M^{-1}$, greater than $10^8$ $M^{-1}$, greater than $10^9$ $M^{-1}$, greater than $10^{10}$ $M^{-1}$, usually up to about $10^{12}$ $M^{-1}$, or even up to about $10^{15}$ $M^{-1}$.

The term "stringent assay conditions" as used herein refers to conditions that are compatible to produce binding pairs of nucleic acids, e.g., capture agents and analytes, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental conditions. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO4, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acids are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are deoxyoligonucleotides (i.e., oligonucleotides), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

A specific example of stringent assay conditions is rotating hybridization at a temperature of about 55° C. to about 70° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1×SSC at room temperature and 37° C.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., a known analyte that is of interest, is used synonymously with the term "pre-determined analyte".

The term "array" encompasses the term "microarray" and refers to an ordered array of capture agents for binding to aqueous analytes and the like. An "array" includes any two-dimensional or substantially two-dimensional (as well as a three-dimensional) arrangement of spatially addressable regions (i.e., "features") containing capture agents, particularly polynucleotides, and the like. Any given support may carry one, two, four or more arrays disposed on a surface of a support. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 100 cm$^2$, 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of the same or different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Arrays can be fabricated by depositing (e.g., by contact- or jet-based methods) either precursor units (such as nucleotide or amino acid monomers) or pre-synthesized capture agent. An array is "addressable" when it has multiple regions of different moieties (e.g., different capture agent) such that a region (i.e., a "feature" or "spot" of the array) at a particular predetermined location (i.e., an "address") on the array will detect a particular sequence. An "array layout" refers to one or more characteristics of the features, such as feature positioning on the support, one or more feature dimensions, and an indication of a moiety at a given location. "Interrogating" the array refers to obtaining information from the array, especially information about analytes binding to the array. "Hybridization assay" references a process of contacting an array with a mobile phase containing analyte. An "array support" refers to an article that supports an addressable collection of capture agents.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. "Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region may be paired with its complementary base, i.e. following normal base-pairing rules. "Substantial sequence complementarity" permits one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The region that is complementary between a first polynucleotide and a second polynucleotide (e.g. a target analyte and a capture agent) is typically at least about 10 bases long, more typically at least about 15 bases long, still more typically at least about 20 bases long, or at least about 25 bases long. In various typical embodiments, the region that is complementary between a first polynucleotide and a second polynucleotide (e.g. target analyte and a capture agent) may be up to about 200 bases long, or up to about 120 bases long, up to about 100 bases long, up to about 80 bases long, up to about 60 bases long, or up to about 45 bases long.

"Reaction vessel" references any container for holding a solution, e.g. a test tube, a well in a multi-well plate, a reaction chamber, a fluid reservoir, a cuvette, a vial, a flask, or any other container for capable of holding a solution. The reaction vessel may be sealed (totally enclosing the solutions), or may be open (allowing the solution to exit the reaction vessel), or may be adapted for being opened or sealed.

Figure 1:
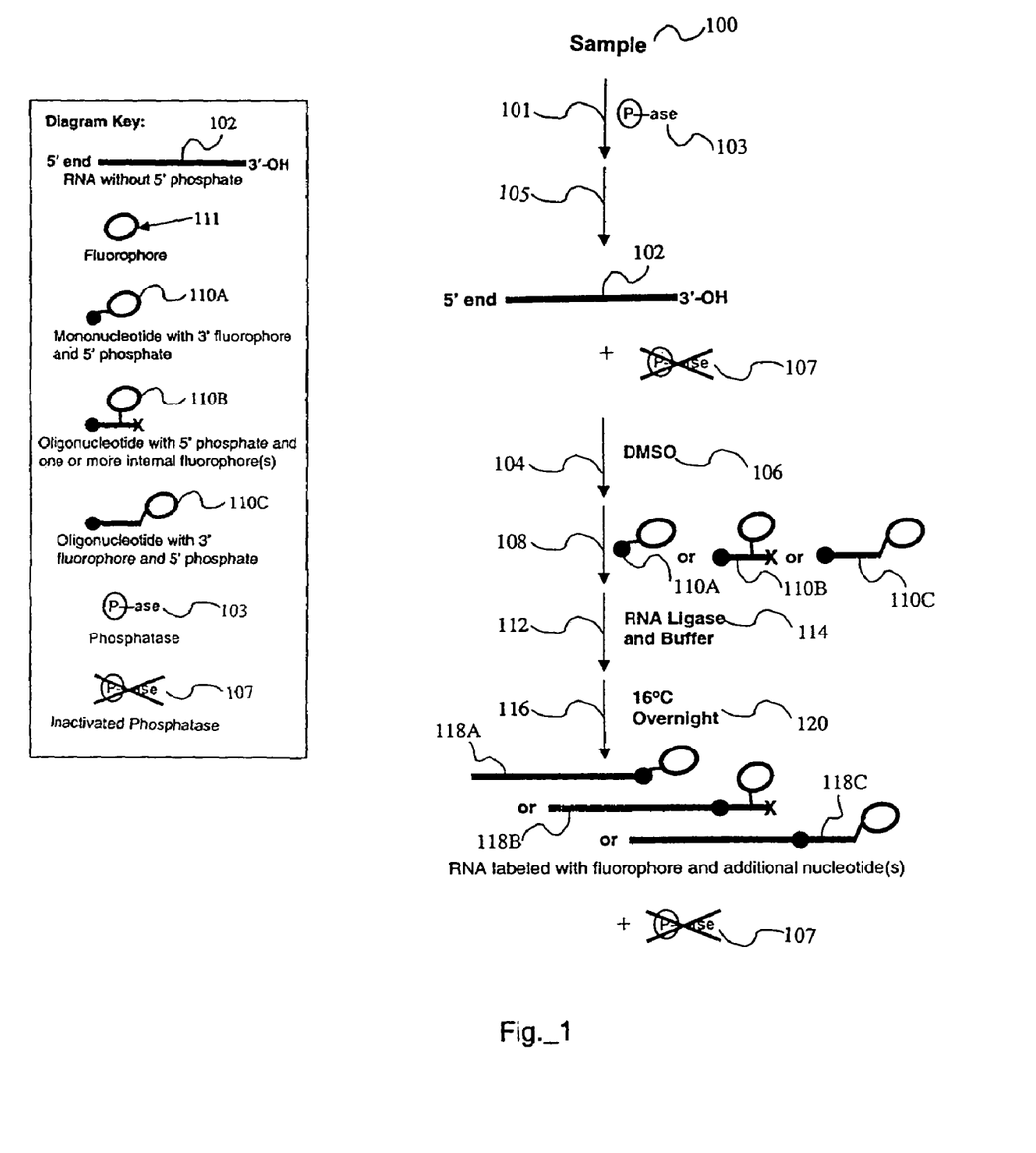

"Upstream" as used herein refers to the 5' direction along a polynucleotide, e.g. an RNA molecule. "Downstream" refers to the 3' direction along the polynucleotide. Hence, a label downstream of an analyte is located at (or is bound to) a nucleotide moiety that is located in the 3' direction from the analyte, e.g. bound to the 3' end of the analyte. Similarly, an "upstream label" references a label that is located at (or is bound to) a nucleotide moiety that is located in the 5' direction from the analyte, e.g. bound to the 5' end of the analyte. "3'-" and "5'-" have their conventional meaning as known in the art. A 5'-phosphate is a phosphate group located at the 5'-end of a polynucleotide. A 3'-hydroxyl is a hydroxyl group located at the 3'-end of a polynucleotide. As an example, FIG. 1 illustrates downstream labeling of an analyte. If the polynucleotide is double stranded, one of the strands is selected as the reference strand, e.g. the strand that is labeled, or the strand that is not labeled (or some other criteria or feature of the strand may be used to designate one strand as the reference strand).

Accordingly, in one embodiment of the present invention, a method of labeling RNA in a sample is provided. Typical embodiments in accordance with the present invention provide methods in which a sample including RNA is contacted with an enzyme having RNA phosphatase activity to provide dephosphorylated RNA. The enzyme having RNA phosphatase activity is then inactivated to provide a resultant solution including the dephosphorylated RNA and inactivated enzyme, the inactivated enzyme no longer having RNA phosphatase activity. The resultant solution is contacted with an enzyme having an RNA ligation activity in the presence of a labeled substrate. This is done under conditions sufficient to result in coupling of the labeled substrate to the RNA in the sample to provide labeled RNA.

In typical embodiments, the resultant solution is contacted with the enzyme having RNA ligation activity under conditions that include a DMSO concentration in the range from about 20% to about 30%. The dimethylsulfoxide (DMSO) concentration is calculated as volume (e.g. in milliliters) of DMSO divided by total volume (e.g. in milliliters) of the solution containing the DMSO. This quantity is typically cast as a percentage by multiplying by 100%. For example, in certain embodiments, the DMSO concentration will be in a range of 20% to about 30%, calculated as the volume of DMSO in the solution resulting from contacting the sample with an enzyme having an RNA ligation activity in the presence of a labeled substrate, divided by the total volume of the solution, and then multiplying by 100%. The other components present in the solution will typically be water, buffer components, salt, RNA, labeled substrate, and enzyme having an RNA ligation activity, although other components may also be present.

The sample may be any RNA sample, typically a sample containing RNA that has been isolated from a biological source, e.g. any plant, animal, yeast, bacterial, or viral source, or a non-biological source, e.g. chemically synthesized. In particular embodiments, the sample includes small RNAs, especially RNAs less than about 500 bases long, e.g. less than about 400 bases long, less than about 300 bases long, less than about 200 bases long, or less than about 100 bases long. In particular embodiments, the sample includes one or more short RNAs, such as e.g. short interfering RNAs (siRNAs), microRNAs (miRNA), tiny non-coding RNAs (tncRNA) and small modulatory RNA (smRNA). See Novina et al., Nature 430: 161-164 (2004). In particular embodiments, the sample includes isolated small RNAs, e.g. the sample results from an isolation protocol for small RNA such as one or more of those listed in this paragraph. In certain embodiments, the small RNA targets may include isolated miRNAs, such as those described in the literature and in the public database (which may be accessed by typing "www" followed by ".sanger-.ac.uk/cgi-bin/Rfam/mirna/browse.pl" into the address bar of a typical internet browser). In particular embodiments, the sample includes isolated small RNAs, e.g. the sample results from an isolation protocol for small RNA, especially RNAs less than about 500 bases long, e.g. less than about 400 bases long, less than about 300 bases long, less than about 200 bases long, less than about 100 bases long, or less than about 50 bases long.

The enzyme having RNA phosphatase activity is typically any RNA phosphatase enzyme, e.g. any RNA phosphatase enzyme capable of removing the 5'-phosphate from a polynucleotide having a 5'-phosphate group. Exemplary enzymes include calf intestinal alkaline phosphatase (Amersham Biosciences, Pittsburgh, Pa.), antarctic alkaline phosphatase (New England Biolabs, Ipswich, Mass.), and shrimp phosphatase (Amersham Biosciences, Pittsburgh, Pa.), or any other RNA phosphatase enzyme capable of removing the 5'-phosphate from a polynucleotide having a 5'-phosphate group. Selection of the enzyme having an RNA phosphatase activity will typically be based on availability of the enzyme and activity of the enzyme under the desired reaction conditions for the dephosphorylation reaction (e.g. temperature, pH, ionic strength, source of RNA and/or labeled substrate, structural feature of RNA and/or labeled substrate, concentration of RNA and/or labeled substrate, presence of other materials (e.g. contaminants, salt, surfactant, other solvents) etc.) In particular embodiments, the enzyme having RNA phosphatase activity is calf intestinal alkaline phosphatase.

The step of contacting the sample including RNA with an enzyme having RNA phosphatase activity to provide dephosphorylated RNA is conducted under conditions sufficient to result in cleavage of 5'-phosphate groups from the RNA in the sample. The conditions of the cleavage (dephosphorylation) reaction will generally be selected with regard to the known (previously described) conditions for use of the particular enzyme chosen for use in the methods of the invention. Experimental parameters may be selected based on known ranges for the experimental parameters or determined through routine experimentation based on, e.g. efficacy of the dephosphorylation reaction. Such other experimental parameters may include, e.g. temperature, pH, ionic strength, source of RNA and/or labeled substrate, structural feature of RNA and/or labeled substrate, concentration of RNA and/or labeled substrate, presence of other materials (e.g. contaminants, salt, surfactant, other solvents) etc.

After the sample including RNA is contacted with an enzyme having RNA phosphatase activity to provide dephosphorylated RNA, the enzyme having RNA phosphatase activity is inactivated. In this regard, "inactivated" means that the enzyme is treated to render the enzyme non-functional, i.e. to substantially eliminate the RNA phosphatase activity of the enzyme. "Substantially eliminate" references a loss of at least about 95% of the activity of the enzyme, e.g. at least about 98%, at least about 99%, or about 100% of the activity of the enzyme. The inactivation may be accomplished using any method that renders the enzyme having RNA phosphatase activity non-functional while not interfering with the remainder of the method. Typical methods for inactivating the enzyme having RNA phosphatase activity include heating the enzyme having RNA phosphatase activity, freezing the enzyme having RNA phosphatase activity, or contacting the enzyme having RNA phosphatase activity with a chemical denaturant, or combinations thereof.

Inactivating the enzyme having RNA phosphatase activity by heating typically includes heating the solution containing the enzyme having RNA phosphatase activity and the dephosphorylated RNA to a temperature in the range of about 65° C. to about 105° C., although temperatures outside the indicated range may be used in certain embodiments. Most typically, the solution containing the enzyme having RNA phosphatase activity and the dephosphorylated RNA is heated to a temperature about 100° C., e.g. by placing a reaction vessel containing the solution in a heat block or in a boiling water bath. In certain embodiments, e.g. in which the enzyme selected is antarctic alkaline phosphatase, a lower temperature may be employed, e.g. about 70° C. In practice, the solution containing the enzyme having RNA phosphatase activity and the dephosphorylated RNA is typically maintained at the desired temperature for a period of about 1 to 30 minutes (e.g. 2 to about 15 minutes, 3 to about 10 minutes), although time periods outside the indicated range may be used in certain embodiments. Generally, longer times may be needed if lower temperatures are employed.

Inactivating the enzyme having RNA phosphatase activity by freezing typically includes cooling the solution containing the enzyme having RNA phosphatase activity and the dephosphorylated RNA to a temperature in the range of about −80° C. to about 0° C., although temperatures outside the indicated range may be used in certain embodiments. Most typically, the solution containing the enzyme having RNA phosphatase activity and the dephosphorylated RNA is frozen to a temperature in the range of about −40° C. to about −5° C., e.g. by placing a reaction vessel containing the solution in an electric freezer, a cooler with finely chopped dry ice, a dry ice/ethanol bath, or any other known method for freezing a solution. In certain embodiments, the solution containing the enzyme having RNA phosphatase activity and the dephosphorylated RNA may undergo several (e.g. in the range of 2 to about 6, e.g. 3, 4, or 5) freeze/thaw cycles, in which the solution is first frozen, then thawed, then re-frozen, etc. In practice, the solution containing the enzyme having RNA phosphatase activity and the dephosphorylated RNA is typically maintained at the desired temperature for a period of about 1 to 30 minutes, although time periods outside the indicated range may be used in certain embodiments, for example, the frozen solution may be stored overnight in certain embodiments. In certain embodiments, both heating and freezing may be used for inactivating the enzyme having RNA phosphatase activity, e.g. the solution containing the enzyme having RNA phosphatase activity and the dephosphorylated RNA may first be heated as described above for a desired period of time and then frozen as described above for a desired period of time.

In certain embodiments, inactivating the enzyme having RNA phosphatase activity may involve contacting the solution containing the enzyme having RNA phosphatase activity and the dephosphorylated RNA with a protein denaturing agent, such as guanidine, a guanidine derivative, urea, a urea derivative, a detergent (e.g. sodium dodecyl sulfate, or a TRITON detergent), or other denaturant. Such protein denaturing agents are well known. The protein denaturing agent will be present in an amount effective to denature the enzyme having RNA phosphatase activity, thus providing a resultant solution including the dephosphorylated RNA and inactivated enzyme, the inactivated enzyme no longer having RNA phosphatase activity. Generally, after the enzyme having RNA phosphatase activity is inactivated, the solution containing the inactivated enzyme, the protein denaturing agent, and the dephosphorylated RNA will be diluted to reduce the concentration of protein denaturing agent, so that the enzyme having RNA ligation activity may still couple the labeled substrate to the dephosphorylated RNA. Thus, the protein denaturing agent and the conditions for its use should be selected such that the protein denaturing agent may be present at a level high enough to inactivate the enzyme having RNA phosphatase activity, but, upon dilution, will still permit the enzyme having RNA ligation activity to retain its activity. For example, if 5% denaturant is effective to denature the enzyme having RNA phosphatase activity, and if the enzyme having RNA ligation activity retains its activity at 1% denaturant, then a dilution of at least 5× may be employed.

In some embodiments, inactivating the enzyme having RNA phosphatase activity may involve use of a protein denaturing agent in combination with heating or freezing, or both. For example, a solution containing the enzyme having RNA phosphatase activity and the dephosphorylated RNA may be contacted with a protein denaturing agent and then heated to a temperature in the range from about 65° C. to about 105° C. Inactivation of the enzyme may be more effective upon heating in the presence of the protein denaturation agent, as compared to heating in the absence of the protein denaturation agent. Similarly, in certain embodiments, a solution containing the enzyme having RNA phosphatase activity and the dephosphorylated RNA may be contacted with a protein denaturing agent and then frozen. Inactivation of the enzyme may be more effective upon freezing in the presence of the protein denaturation agent, as compared to freezing in the absence of the protein denaturation agent.

The inactivation of the enzyme having RNA phosphatase activity provides a resultant solution that includes the dephosphorylated RNA and inactivated enzyme, the inactivated enzyme no longer having RNA phosphatase activity. In certain embodiments, the resultant solution is adjusted to a temperature in the range of about 0° C. to about 10° C., for a time period of about 1 minute to about 30 minutes, or even longer. In certain embodiments, the resultant solution may be frozen and stored for later use.

In certain embodiments, after the inactivation of the enzyme having RNA phosphatase activity and before the resultant solution is contacted with the enzyme having an RNA ligation activity, the method includes adding DMSO to the resultant solution and then heating the resultant solution. In this optional heating step, the resulting solution is typically heated to a temperature of at least about 80° C. (e.g. at least about 85° C., at least about 90° C., at least about 95° C.; and up to about 105° C. or 110° C.) under conditions that include a DMSO concentration of at least about 40% DMSO (typically up to about 60% DMSO, although in some embodiments the DMSO concentration may be up to 70% DMSO, up to 80% DMSO, or even more). This optional heating is maintained for at least 10 seconds, typically at least about 20 seconds, at least about 30 seconds, at least about 1 minute, at least about 2 minutes, and up to about 15 minutes, or more. In particular embodiments, reaction solutions of up to about 50 microliters are heated for about 30 to about 60 seconds per 5-10 microliters of reaction solution. After the heating, the RNA is typically quickly cooled (e.g. to less than about 40° C., more typically less than about 20° C., or in some embodiments less than about 5° C.) before adding the enzyme having an RNA ligation activity.

The enzyme having an RNA ligation activity is typically any RNA ligase enzyme, although other enzymes capable of coupling the labeled substrate to the RNA may be used. In particular embodiments, the enzyme having an RNA ligation activity is capable of coupling a nucleotide (or oligonucleotide, or RNA) having a 5' phosphate to an oligonucleotide having a 3' hydroxyl. Exemplary enzymes include T4 RNA ligase available from Amersham/Pharmacia company, THERMOPHAGE™ RNA ligase II (available from Prokaria LTD, Iceland), or other available RNA ligase enzymes known to be capable of coupling a nucleotide (or oligonucleotide, or RNA) having a 5' phosphate to an oligonucleotide having a 3' hydroxyl. In certain embodiments, the enzyme may be selected from yeast poly A polymerase, *E. coli* poly A polymerase, or terminal transferase (each of which is available from Amersham/Pharmacia). The enzyme having an RNA ligation activity should be selected such that the enzyme is capable performing the coupling when one (or both) of the nucleotide (or oligonucleotide) having a 5' phosphate and/or the oligonucleotide having a 3' hydroxyl includes a label. Selection of the enzyme having an RNA ligation activity will typically be based on availability of the enzyme and activity of the enzyme under the desired reaction conditions for the coupling (e.g. temperature, pH, ionic strength, source of RNA and/or labeled substrate, structural feature of RNA and/or labeled substrate, concentration of RNA and/or labeled substrate, presence of other materials (e.g. contaminants, salt, surfactant, denaturing agent, other solvents) etc.)

The coupling reaction is conducted under conditions sufficient to result in coupling of the labeled substrate to the dephosphorylated RNA to provide labeled RNA. The conditions of the coupling reaction will generally be selected with regard to the known (previously described) conditions for use of the particular enzyme chosen for use in the methods of the invention, with the specific modifications described herein. In particular embodiments, the DMSO concentration of the reaction mixture for the coupling reaction will be in the range of 20% to 30%. Other experimental parameters may be selected based on known ranges for the experimental parameters or determined through routine experimentation based on, e.g. efficacy of the labeling reaction. Such other experimental parameters may include, e.g. temperature, pH, ionic strength, source of RNA and/or labeled substrate, structural feature of RNA and/or labeled substrate, concentration of RNA and/or labeled substrate, presence of other materials (e.g. contaminants, salt, surfactant, denaturing agent, other solvents) etc.

This coupling reaction is carried out in the presence of the inactivated enzyme which is present in the reaction mixture from the preceding dephosphorylation reaction and inactivation of the enzyme having RNA phosphatase activity. Thus, the subject methods do not involve a step in which the dephosphorylated RNA is physically separated from the inactivated enzyme (at least not until after the coupling reaction, as described herein). Thus, the coupling reaction is carried out in the presence of the inactivated enzyme that is unable to catalyze dephosphorylation of RNA, at least for the duration of the coupling step. As a result, the inactive enzyme cannot act upon the labeled substrate to cause dephosphorylation of the labeled substrate.

In typical embodiments, the resultant solution is kept in the same reaction vessel during the steps of: contacting the sample including RNA with the enzyme having RNA phosphatase activity; inactivating the enzyme having RNA phosphatase activity; and contacting the resultant solution with an enzyme having an RNA ligation activity in the presence of a labeled substrate. In typical embodiments, in the time period between when the dephosphorylated RNA is provided and when the labeled RNA is provided, no RNA precipitation step is performed, and no desalting step is performed.

The labeled substrate comprises an observable label moiety attached to a nucleotide moiety. The nucleotide moiety is typically a mononucleotide moiety or an oligonucleotide moiety. In particular embodiments, the nucleotide moiety is less than about 100 bases long. In certain embodiments the nucleotide moiety will typically be at least three bases long. In certain embodiments, the nucleotide moiety will be less than 50 bases long, e.g. less than 40 bases long, less than 30 bases long, less than 20 bases long. In some embodiments, the nucleotide moiety will be 1, 2, 3, 4, 5, or 6 bases long. The nucleotide moiety may typically have any desired sequence or even an unknown sequence. In certain embodiments, a plurality of labeled substrates may be used in the same reaction (e.g. a plurality of nucleotide moieties, each having a different sequence, each having an observable label moiety attached), thereby resulting in ligating one of a plurality of nucleotide moieties to each molecule of RNA.

The observable label moiety is a moiety that provides for an observable signal that indicates the presence of the observable label moiety. Typical examples include a chromogenic moiety, a fluorophore, a mass label, a spin label, a radiolabel, or other labels known in the art. In particular embodiments, the observable label moiety is a fluorophore selected from the group consisting of Cy3, Cy5, and an Alexa dye. Further examples of label moieties include any commercially available fluorophores that can be conjugated to mononucleotides or polynucleotides, e.g. dyes from Molecular Probes (Eugene, Oreg. and Leiden, The Netherlands) such as the Alexa Fluor series (example: Alexa 350, Alexa 430, Alexa 532, Alexa 546, Alexa 568, and Alexa 594) and the series of BODIPY conjugates. Other examples include: Tamra, Fluorescein, carboxyfluorescene, JOE, rhodamine, carboxyrhodamine, CY series, Oyster series. More information about commercially available dyes for oligonucleotide conjugation can be found at the website accessed by typing "http://www" followed by ".synthegen.com" in to the address bar of a typical web browser. Any such dyes may potentially be used in accordance with the methods described herein. Although the examples described herein use a fluorophore as the label, it will be apparent to those of ordinary skill that other labels may be used (instead of a fluorophore, or even in addition to a fluorophore). Such labels typically are well known in the art.

The observable label moiety may be attached to the nucleotide moiety at any site of the nucleotide moiety that is compatible with the ligation reaction. In other words, the label moiety should not prevent the ligation reaction, e.g. by interfering with the enzyme having an RNA ligation activity. In certain embodiments, the label moiety may be attached to the nucleotide moiety via the 3'-site at the end of the nucleotide moiety or may be attached at any available "internal" site (i.e. other than the 3'-site or 5'-site) of the nucleotide moiety. The observable label moiety could be incorporated as a special phosphoramidite during the oligoribonucleotide synthesis or as a post-synthetic modification. An example of the phosphoramidite method includes direct coupling of label-containing phosphoramidite during synthesis of the oligonucleotide moiety, or the incorporation of amino-activated phosphoramidite during synthesis of the oligonucleotide moiety, which enables post-synthetic coupling to a desired observable label moiety. In particular embodiments, the observable label moiety is attached to the nucleotide moiety via a linking group, wherein the linking group may be attached to the nucleotide moiety via a 3' terminus of the nucleotide moiety or any other available site of the nucleotide moiety. The linking group may be any linking group known in the art that does not prevent the ligation reaction (e.g. does not prevent the enzyme having an RNA ligation activity from ligating the RNA and the labeled substrate). Any such linking groups or other means of attachment of the label moiety to the nucleotide moiety known in the art may provide for the labeled substrate.

Thus, in particular embodiments, the labeled substrate has the structure:

N-D wherein: N is selected from a mononucleotide moiety or an oligonucleotide moiety having a length of less than about 100 bases, and D is an observable label moiety (e.g. attached to N via a 5' terminus or a 3' terminus of N, or any other available site of N).

An embodiment of a method in accordance with the present invention is illustrated in FIG. 1. In FIG. 1, the method of labeling RNA includes contacting 101 a sample 100 containing RNA with an enzyme having RNA phosphatase activity 103 to provide dephosphorylated RNA 102. The enzyme having RNA phosphatase activity 103 is then inactivated 105 to provide a resultant solution including the dephosphorylated RNA 102 and inactivated enzyme 107, the inactivated enzyme 107 no longer having RNA phosphatase activity. In typical embodiments, DMSO 106 is added 104. Optionally, the mixture may be briefly heated (e.g. for about 1 to about 10 minutes) and then quickly cooled down. The labeled substrate 110A, 110B or 110C may then be added 108 to the mixture (containing the DMSO 106, the dephosphorylated RNA 102, and the inactivated enzyme 107). The labeled substrate 110A, 110B or 110C typically is a mononucleotide with a 3' fluorophore and 5' phosphate 110A, an oligonucleotide with a 5' phosphate and one or more internal fluorophore(s) 110B, or an oligonucleotide with a 3' fluorophore and 5' phosphate 110C. (In an embodiment in which the labeled substrate 110B has one or more internal fluorophores, the 3' end of the oligonucleotide lacks the 3' hydroxyl, as indicated by the 'X' in FIG. 1. For example, a periodate oxidation reaction may be used to modify the 3' end, or the 3' end may be modified by having a fluorophore bound thereto.) The enzyme having an RNA ligation activity 114 is also added 112. In typical embodiments, the concentrations of the solutions and the volumes added are planned to provide that the resulting solution has the desired concentration of DMSO (e.g. in the range of about 20% to about 30%, more typically in the range of about 22% to about 28%, even more typically in the range of about 24% to about 26%). The reaction solution (including the inactivated enzyme 107) is then allowed to react 116 under conditions and for a time sufficient for the coupling of the labeled substrate to the RNA to occur, thereby providing the labeled RNA 118A, 118B, or 118C, in a solution that includes the inactivated enzyme 107. Typical conditions 120 of overnight incubation at 16° C. are shown for the embodiment of FIG. 1, although these conditions may vary depending on the particular enzyme used and the RNA and labeled substrate provided. Further steps to work up the labeled RNA may then be performed, e.g. a purification of the labeled RNA, e.g. by alcohol precipitation, by size exclusion chromatography, by desalting, or any other known clean-up methods. In the illustrated embodiment, the label is a fluorophore 111, but other labels may be used as long as the coupling of the labeled substrate to the RNA may still occur. Selection and optimization of the conditions is within routine experimentation for one of ordinary skill in the art given the disclosure herein.

In the embodiment illustrated in FIG. 1, the labeled substrate denominated 110A is shown as a mononucleotide attached to a fluorophore. In other embodiments illustrated in FIG. 1, the labeled substrates 110B and 110C are shown as an oligonucleotide having one or more fluorophore(s) attached to the oligonucleotide, in which the oligonucleotide does not have a 3' hydroxyl. The lack of the 3' hydroxyl helps prevent concatenation of the labeled substrate. The labeled substrate 110C is shown as an oligonucleotide having a fluorophore(s) attached to an oligonucleotide at the 3' end of the oligonucleotide. In certain embodiments, the labeled substrate includes an oligonucleotide having attached thereto a plurality, e.g. 2, 3, 4, 5, or more label moieties, up to about 10, 20, 30 or more label moieties, attached to the oligonucleotide moiety at internal (not terminal) sites. In certain such embodiments, a label moiety is also attached to the oligonucleotide via the 3' terminal carbon of the oligonucleotide.

In particular embodiments, the enzyme having an RNA ligation activity catalyzes a coupling reaction between a donor molecule having a 5'-phosphate and an acceptor molecule having a 3'-hydroxyl, as shown in the reaction:

Where:
Acc-3'-OH is the acceptor molecule having a 3'-hydroxyl;
PO$_4$-5'-Don is the donor molecule having a 5'-phosphate;
Acc-3'-O—PO$_3$-5'-Don is the product having the coupled donor and acceptor moieties (e.g. the labeled RNA); and
(enz) is the enzyme having an RNA ligation activity.

In typical embodiments, such as that illustrated in FIG. 1, the acceptor molecule is the RNA 102 and the donor molecule is the labeled substrate 110A, 110B or 110C. The resulting product 118A, 118B, or 118C has the labeled substrate moiety downstream from the RNA, i.e. the product is a downstream labeled RNA.

It should be noted that the general utility of the method is not limited to the particular sequence of steps shown in FIG. 1 or otherwise explicitly mentioned herein. Other sequences of steps leading to essentially similar results are intended to be included in the invention. For example, in certain embodiments, the labeled substrate may be dissolved in a solution that includes the DMSO, and the mixture added to the dephosphorylated RNA and inactivated enzyme prior to contacting with the enzyme having an RNA ligase activity. Thus, in particular embodiments, the invention includes any process which results in contacting the resultant solution with the enzyme having an RNA ligation activity in the presence of the labeled substrate and the inactivated enzyme (i.e. the enzyme that no longer has RNA phosphatase activity), e.g. under conditions which include a DMSO concentration in the range from about 20% to about 30%.

With reference to FIG. 1, in certain embodiments, after the DMSO 106 is added 104 and before the enzyme having an RNA ligation activity 114 is added 112, the method 100 includes heating the resultant solution containing the dephosphorylated RNA 102 and the inactivated enzyme 107 in the presence of the added DMSO 106. In this optional heating step, the solution is typically heated to a temperature of at least about 80° C. (e.g. at least about 85° C., at least about 90° C., at least about 95° C.; and up to about 105° C. or 110° C.) under conditions that include a DMSO concentration of at least about 20% DMSO, e.g. at least about 30% DMSO, at least about 40% DMSO (typically up to about 60% DMSO, although in some embodiments the DMSO concentration may be up to 70% DMSO, up to 80% DMSO, or even more). This optional heating is maintained for at least 10 seconds, typically at least about 20 seconds, at least about 30 seconds, at least about 1 minute, at least about 2 minutes, and up to about 15 minutes, or more. In particular embodiments, reaction solutions of up to about 50 microliters are heated for about 30 to about 60 seconds per 5-10 microliters of reaction solution. After the heating, the RNA is typically quickly cooled (e.g. to less than about 40° C., more typically less than about 20° C., or in some embodiments less than about 5° C.) before adding the enzyme having an RNA ligation activity.

In some embodiments, the labeled substrate has only one observable label moiety attached to the nucleotide moiety. In such embodiments, the labeled RNA will consist essentially of RNA labeled with a single label moiety (i.e. each labeled RNA molecule will have only one observable label moiety attached—referenced herein as "singly-labeled RNA"). This potentially provides increased ease of use in quantitative methods using the labeled RNA.

In other embodiments, the nucleotide moiety of the labeled substrate has a plurality of observable label moieties. In such embodiments, when the labeling reaction is performed to yield the labeled RNA, each labeled RNA molecule will have a plurality of observable label moieties (referenced herein as "multiply-labeled RNA"). Thus, the labeled RNA will consist essentially of RNA labeled with a plurality of label moieties. This increased labeling of the RNA may provide for greater sensitivity in analyses using the labeled RNA. In particular embodiments, each labeled RNA molecule in the sample will be labeled with a consistent number of observable label moieties (relative to the other labeled RNA molecules in the sample). This provides opportunity for more quantitative analysis of labeled RNA than in methods that provide an inconsistent number of observable labels per labeled RNA molecule.

In certain embodiments, methods of performing an array analysis of an RNA sample are provided. In certain embodiments, the invention provides a method of performing an array analysis wherein the method includes labeling the RNA in the sample to provide labeled RNA using a labeling method in accordance with the methods described herein. The labeled RNA is then contacted with an array under conditions sufficient to provide for specific binding of labeled RNA to the array. The array typically is then interrogated to provide data on binding of the labeled RNA to the array.

Standard hybridization techniques (using stringent hybridization conditions) are used to hybridize a labeled sample to a nucleic acid array. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol 7, pgs 43-65 (Plenum Press, New York 1985). See also U.S. Pat. Nos. 6,335,167; 6,197,501; 5,830,645; and 5,665,549; the disclosures of which are herein incorporated by reference. Hybridizing the sample to the array is typically performed under stringent hybridization conditions, as described herein and as known in the art. Selection of appropriate conditions, including temperature, salt concentration, polynucleotide concentration, time (duration) of hybridization, stringency of washing conditions, and the like will depend on experimental design, including source of sample, identity of capture agents, degree of complementarity expected, etc., and are within routine experimentation for those of ordinary skill in the art to which the invention applies.

Following hybridization, the array-surface bound polynucleotides are typically washed to remove unbound and not tightly bound labeled nucleic acids. Washing may be performed using any convenient washing protocol, where the washing conditions are typically stringent, as described above.

Following hybridization and washing, as described above, the hybridization of the labeled target nucleic acids to the capture agents is then detected using standard techniques of reading the array, i.e. the array is interrogated. Reading the resultant hybridized array may be accomplished by illuminating the array and reading the location and intensity of resulting fluorescence at each feature of the array to detect any binding complexes on the surface of the array. For example, a scanner may be used for this purpose, which is similar to the Agilent microarray scanner available from Agilent Technologies, Palo Alto, Calif. Other suitable devices and methods are described in U.S. Pat. No. 6,756,202 entitled "Reading Multi-Featured Arrays" by Dorsel et al.; and U.S. Pat. No. 6,406,849. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, results from interrogating the array are used to assess the level of binding of the population of labeled nucleic acids to capture agents on the array. The term "level of binding" means any assessment of binding (e.g. a quantitative or qualitative, relative or absolute assessment) usually done, as is known in the art, by detecting signal (i.e., pixel brightness) from a label associated with the sample nucleic acids, e.g. the digested sample is labeled. The level of binding of labeled nucleic acid to capture agent is typically obtained by measuring the surface density of the bound label (or of a signal resulting from the label).

In certain embodiments, a surface-bound polynucleotide may be assessed by evaluating its binding to two populations of nucleic acids that are distinguishably labeled. In these embodiments, for a single surface-bound polynucleotide of interest, the results obtained from hybridization with a first population of labeled nucleic acids may be compared to results obtained from hybridization with the second population of nucleic acids, usually after normalization of the data. The results may be expressed using any convenient means, e.g., as a number or numerical ratio, etc.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Experimental Methods

Stock solutions of 20 µM RNA oligonucleotides were stored in 1×TE (10 mM Tris-HCl, pH 7.5, 1 mM EDTA). The reactions containing 25% DMSO were assayed with and without the pre-heating with DMSO step. For resultant solutions that were pre-heated with DMSO, the heated mixtures contained 40-70% DMSO and were heated using a 104° C. heating block for 1.5-2 minutes. The heated samples were immediately set on ice for >5 minutes prior to final assembly.

The final ligation reaction contains the dephosphorylated RNA, the inactivated enzyme (i.e. the enzyme that no longer has the phosphatase activity), buffer (50 mM Tris-HCl, pH 7.5, 10 mM MgCl$_2$, 10 mM DTT, 1 mM ATP, 60 ng/µL BSA), 1 unit/µL T4 RNA ligase, 100 µM 5'-phosphate-cytidyl-phosphate-Cy5-3' (pCpCy5) or 5'-phosphate-cytidyl-phosphate-Cy3-3'(pCpCy3) (Dharmacon) and 2-4 µM RNA oligonucleotides. The reactions are incubated at 16° C. overnight. The RNA ligase is inactivated by heating the reaction solutions using a 104° C. heating block for 1.5-2 minutes, followed by immediately setting on ice for >5 minutes.

The labeling efficiency was determined by 5'-phosphorylation of RNA ligation reaction aliquots with radioactive $P^{32}$-gamma-ATP. The resulting mixture was desalted with Micro Bio-Spin™ (BioRad) desalting columns. The desalted mixture was loaded onto denaturing polyacrylamide gel. Since the ligation products contain an extra nucleotide and fluorophore, they have a lower electrophoretic migration rate than the unligated precursors. $P^{32}$-labeled RNA bands are visualized and quantified with phosphorimager (Molecular Dynamics). The ligation efficiency was determined by the ratio of ligated vs. unligated $P^{32}$-labeled RNA bands. Thus, ligation efficiency may be expressed as the mol % of initial RNA that winds up having an attached label moiety.

Description of Labeling Protocol:

A sample containing RNA is first dephosphorylated using phosphatase, preferably calf intestine phosphatase (Amersham), but other phosphatases can be used as well, such as antarctic alkaline phosphatase (New England Biolabs) or shrimp phosphatase (Amersham). Typical conditions include buffer of 50 mM Tris (pH 9), 1 mM MgCl$_2$; 0.3-1.6 units/µl phosphatase; 37° C. for 30 minutes; RNA 1-10 ng/µl, e.g. 1 ng/µl to 15 ng/µl.

In various embodiments, any compatible buffer in the pH range compatible with enzyme activity and RNA stability may be employed, typical ranges of buffer concentration is 10-100 mM, but may be outside that range in certain embodiments. The pH is in a range compatible with enzyme activity, typically in the range of 5 to about 10.5, more typically in the range of about 6 to about 10, e.g. about 7 to about 9.5, e.g. about 8 to about 9. The pH will typically be determined based on choice of enzyme and buffer. The buffer may include other components, such as salts, e.g. 1 mM MgCl$_2$, compatible with activity of the enzyme.

The phosphatase enzyme will be present in an amount sufficient to efficiently dephosphorylate the RNA. The amount of phosphatase enzyme may vary depending on desired reaction conditions, but will typically be in the range from 0.2 units/µl to about 10 units/µl, e.g. 0.3 to about 5 units/µl, e.g. 0.4 units/µl to about 3 units/µl, but may be outside the indicated ranges in certain embodiments. The RNA concentration is typically in the range of 0.1 to about 100 ng/µl, e.g. 1 to about 40 ng/µl, e.g. 1 ng/µl to 15 ng/µl, but may be outside the indicated ranges in certain embodiments.

The dephosphorylation is terminated by inactivation of the phosphatase by heating at 100° C. for 4-5 min. If antarctic alkaline phosphatase or shrimp phosphatase is used instead, heat inactivation can be done at 70° C. for 10 minutes. The heat inactivation is terminated by immediately cooling the samples by putting the sample tubes on ice or ice water. After cooling, DMSO is added to the sample to 40% of the total volume. This DMSO mixture is then mixed and heated 2-4 minutes 100° C. The heating is terminated by immediate cooling by placing the reaction vessel containing the resultant solution over ice.

The mixture is now assembled for ligase labeling with pCp-Dye. In embodiments described here, T4 RNA ligase is used to label synthetic RNA oligonucleotides with 5'-phosphate-cytidyl-phosphate-Cy5-3' (pCp-Cy5) or 5'-phosphate-cytidyl-phosphate-Cy3-3' (pCp-Cy3). The final reaction mixture will contain 1× ligation buffer (example: 0.01% BSA, 50 mM Tris-HCl, pH 7.5, 10 mM $MgCl_2$, 10 mM DTT, 1 mM ATP), ligase, and pCp-Dye. There is no need to desalt or phenol extract after dephosphorylation and before ligase reaction. After the labeling reaction, the labeled RNA can be desalted to remove excess unlabeled dye prior to hybridizing to a microarray.

The ligation reaction conditions described here have been observed to result in ligation efficiencies of about 60% or more, e.g. about 70% or more, or 80% or more, up to about 95% or more, e.g. up to about 99% with minimal sequence discrimination. This was accomplished by reacting at 25% DMSO, 16° C. overnight, with donor to acceptor ratio of >12.5:1. The reaction buffer contains 50 mM Tris-HCl, pH 7.5, 10 mM $MgCl_2$, 10 mM DTT, 1 mM ATP, 60 μg/mL BSA, and 25% DMSO. Typical reactions are 10 μL with 2 μM RNA, 100 μM pCp-Cy5 or pCp-Cy3, and 4 units T4 RNA ligase (Amersham/Pharmacia). Reaction efficiency seemed unaffected by increasing the RNA concentration to 8 μM or decreasing enzyme to 2 units.

In various embodiments, any compatible buffer in the pH range compatible with the ligase enzyme activity and RNA stability may be employed, typical ranges of buffer concentration is 10-100 mM, but may be outside that range in certain embodiments. The pH is in a range compatible with enzyme activity, typically in the range of 5 to about 10.5, more typically in the range of about 6 to about 10, e.g. about 7 to about 9.5, e.g. about 8 to about 9. The pH will typically be determined based on choice of enzyme and buffer. The buffer may include other components, such as salts, e.g. 10 mM $MgCl_2$, compatible with activity of the enzyme. Other components that may be present include bovine serum albumin (e.g. 0.001% to 0.05%), dithiothreitol (e.g. 0.5 to 50 mM), bulk DNA (to block non-specific binding), etc. ATP (e.g. 0.5 to 5 mM) is also included, and the labeled substrate is typically present in a concentration in the range of about 10-500 μM, e.g 50-300 μM. In certain embodiments, any of the listed components may be outside the indicated ranges.

The RNA ligase enzyme will be present in an amount sufficient to efficiently couple the dephosphorylated RNA to the labeled substrate (e.g. the pCp-Dye). The amount of RNA ligase enzyme may vary depending on desired reaction conditions, but will typically be in the range from 0.2 units/μl to about 10 units/μl, e.g. 0.3 to about 5 units/μl, e.g. 0.4 units/μl to about 3 units/μl, but may be outside the indicated ranges in certain embodiments. The RNA concentration is typically in the range of 0.1 to about 100 ng/μl, e.g. 1 to about 40 ng/μl, e.g. 1 ng/μl to 15 ng/μl, but may be outside the indicated ranges in certain embodiments.

Determination of Labeling Efficiency of miRNAs in Complex Samples:

The RNA in a complex RNA mixture, such as the total RNA or isolated mixtures of small RNAs from biological samples, is labeled as described herein. The labeled mixtures are run on denaturing polyacrylamide gel and Northern blots are performed of individual miRNAs with radioactive probes. The RNAs labeled by RNA ligase will have a lower mobility relative to its unlabeled counterpart. Thus each target sequence will run as a doublet when probed by Northern blot. The ratio of RNA species in these doublets reflects the molar ratio of the RNA ligase labeled vs. unlabeled RNA species.

Moreover, it is possible to determine the labeling efficiencies of each individual miRNA of a given set and perform highly quantitative microarray experiments by correlating fluorophore counts with number of molecules. For example, in an array hybridization experiment wherein an array is contacted with labeled RNA, it is possible to ascertain the total quantity of fluorophores in a given area of the array by interrogating (or scanning) the array; given the labeling efficiency of the labeled RNA (determined as disclosed herein), the quantity of RNA hybridized to the given area of the array may be determined. Potentially, the RNA ligase method can be used for dyes other than Cy5 and Cy3, but the efficiency of labeling may vary.

Given that the approximate labeling efficiency may be determined (as described herein), in particular embodiments the present invention thus provides quantitative methods of performing array hybridization experiments. It is expected that this will provide a more sensitive assay system for the detection of variations of miRNA, such as found in developmental stages, tissue samples, disease states, as well as any individual and/or abnormal variations. Moreover, if more viral miRNAs are identified, this can become a novel diagnostic tool for active as well as latent viral infections Microarray Hybridization:

The method set forth herein is used to label RNA in a sample with either Cy5 or Cy3, and the labeled RNA is hybridized onto microarrays as follows:

Labeled RNA is desalted with BioRad™ MICRO BIO-SPIN™ 6 columns (as directed by BioRad instructions) to remove free fluorescent tags. The desalted labeled RNA is added to a solution containing water and carrier (25-mer DNA with random sequence). The solution is heated for approximately 1 minute per 10 ul solution at 100° C. and is immediately placed on ice. After cooling, 2× Agilent Hyb Buffer (1225 mM LiCl, 300 mM Li-MES, pH 6.1, 12 mM EDTA, 3.0% (w/v) lithium dodecyl sulfate, 2.0% (w/v) Triton X-100) is added to the mixture and the viscous liquid mixed carefully. The final solution contains 1×Hyb Buffer and 0.1 μg/μl random 25-mer DNA. The concentration of RNA is varied for different experiments.

Hybridization is performed with SureHyb hybridization chamber (Agilent Part Number:G2534A); the hybridization chamber is placed on the rotisserie of a hybridization oven overnight. The hybridization is performed at a temperature of about 50° C. to about 60° C.

After hybridization is complete, the hybridization chamber complex is removed from the oven and immediately disassembled in Wash Buffer 1 (6×SSC, 0.005% Triton X-102) at room temperature. The microarray is transferred to a fresh wash chamber containing Wash Buffer 1 and is washed by stirring for 10 minutes at room temperature. The microarray is then washed in Wash Buffer 2 (0.1×SSC, 0.005% Triton X-102) by stirring at room temperature for 5 minutes. The microarray is then slowly lifted out of the wash chamber after washing and is dried with nitrogen as needed. The microarray is scanned with Agilent Scanner (Agilent Product Number: G2565BA). The scanned data is extracted with Agilent Feature Extraction Software (Agilent Product Number; G2567AA) and the green and red background-subtracted signals are evaluated for hybridization efficiency and specificity. Data may be further analyzed using Spotfire software and Microsoft Excel.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A method of labeling RNA in a sample comprising:
   a) contacting a sample comprising a plurality of RNAs with calf intestinal alkaline phosphatase under conditions and for a time sufficient to result in dephosphorylated RNA;
   b) mixing the dephosphorylated RNA with DMSO to produce a resultant solution comprising DMSO at a concentration in the range from about 20% to about 70% and heating the resultant solution in a temperature range of about 65° C. to about 100° C., followed by cooling the resultant solution to about 0° C. to about 10° C.;
   c) contacting the resultant solution with an enzyme having RNA ligation activity in the presence of a labeled substrate under conditions sufficient to result in coupling of the labeled substrate to the dephosphorylated RNA to provide labeled RNA, said coupling occurring in the presence of an inactivated calf intestinal alkaline phosphatase no longer having RNA phosphatase activity; and
   wherein no phenol extraction is done after said contacting step a) and before said contacting step c); and wherein steps a), b), and c) all occur in the same reaction vessel.

2. The method of claim 1, wherein the duration of heating of the resultant solution is in the range of about 10 seconds to about 10 minutes.

3. The method of claim 1, wherein the conditions of contacting the resultant solution with the enzyme having RNA ligation activity include a DMSO concentration in the range of about 20% to about 30%.

4. The method of claim 1, wherein the labeled substrate comprises an observable label moiety attached to a nucleotide moiety.

5. The method of claim 4, wherein the nucleotide moiety is selected from a mononucleotide moiety or an oligonucleotide moiety.

6. The method of claim 4, wherein the nucleotide moiety has a length in the range from 2 to about 50 bases.

7. The method of claim 4, wherein the nucleotide moiety has a length in the range from 2 to about 6 bases.

8. The method of claim 4, wherein the observable label moiety is selected from a chromogenic moiety, a fluorophore, a mass label, a spin label, or a radiolabel.

9. The method of claim 4, wherein the observable label moiety is a fluorophore selected from the group consisting Cy3, Cy5, or an Alexa dye.

10. The method of claim 1, wherein the RNA in the sample comprises isolated RNA having length less than 500 bases.

11. The method of claim 1, wherein the RNA in the sample comprises isolated RNA having length less than 200 bases.

12. The method of claim 1, wherein the enzyme having RNA ligation activity is selected from T4 RNA ligase, RNA ligase II, yeast poly A polymerase, *E. coli* poly A polymerase, or terminal transferase.

13. The method of claim 1, wherein the enzyme having RNA ligation activity is T 4 RNA ligase.

* * * * *

UNITED STATES PATENT AND TRADEMARK OFFICE
CERTIFICATE OF CORRECTION

PATENT NO. : 7,700,289 B2  Page 1 of 1
APPLICATION NO. : 11/397067
DATED : April 20, 2010
INVENTOR(S) : Hui Wang It is certified that error appears in the above-identified patent and that said Letters Patent is hereby corrected as shown below:

On the title page, in field (56), under "Other Publications", in column 2, line 9, delete "Pratical" and insert -- Practical --, therefor.

On the title page, in field (56), under "Other Publications", in column 2, line 11, delete "Ularich" and insert -- Ulrich --, therefor.

On the title page, in field (56), under "Other Publications", in column 2, line 12, delete "Praffin" and insert -- Paraffin --, therefor.

On the title page, in field (56), under "Other Publications", in column 2, line 21, delete "Oligoribunucleotides," and insert -- Oligoribonucleotides, --, therefor.

In column 24, line 30, in claim 13, delete "T 4" and insert -- T4 --, therefor.

Signed and Sealed this

Twenty-ninth Day of June, 2010

David J. Kappos
*Director of the United States Patent and Trademark Office*